(12) United States Patent
Kondo et al.

(10) Patent No.: US 9,574,933 B2
(45) Date of Patent: Feb. 21, 2017

(54) TERAHERTZ-WAVE DETECTION ELEMENT, MANUFACTURING METHOD THEREFOR, AND OBSERVATION APPARATUS

(71) Applicant: NGK INSULATORS, LTD., Aichi (JP)

(72) Inventors: Jungo Kondo, Miyoshi (JP); Yuichi Iwata, Nagoya (JP); Tetsuya Ejiri, Kasugai (JP)

(73) Assignee: NGK INSULATORS, LTD., Aichi (JP)

( * ) Notice: Subject to any disclaimer, the term of this patent is extended or adjusted under 35 U.S.C. 154(b) by 100 days.

(21) Appl. No.: 14/665,124

(22) Filed: Mar. 23, 2015

(65) Prior Publication Data

US 2015/0192458 A1 Jul. 9, 2015

Related U.S. Application Data

(63) Continuation of application No. PCT/JP2013/075274, filed on Sep. 19, 2013.

(30) Foreign Application Priority Data

Sep. 24, 2012 (JP) ................. 2012-209412

(51) Int. Cl.
*G01J 1/04* (2006.01)
*G01N 21/3581* (2014.01)
(Continued)

(52) U.S. Cl.
CPC .............. *G01J 1/0407* (2013.01); *G01J 3/021* (2013.01); *G01J 3/42* (2013.01); *G01N 21/3581* (2013.01); *G01N 21/3586* (2013.01); *G02F 1/03* (2013.01)

(58) Field of Classification Search
CPC ............ G01J 1/0407; G01J 3/021; G01J 3/42; G01N 21/3581; G01N 21/3586; G02F 1/03

See application file for complete search history.

(56) References Cited

U.S. PATENT DOCUMENTS 6,894,514 B2 5/2005 Yanagisawa
7,087,294 B2 8/2006 Noda et al.
(Continued)

FOREIGN PATENT DOCUMENTS

JP 2002-337274 A 11/2002
JP 2003-185696 A 7/2003
(Continued)

OTHER PUBLICATIONS

International Search Report for PCT Patent App. No. PCT/JP2013/075274 (Oct. 15, 2013).
(Continued)

*Primary Examiner* — Mark R Gaworecki
(74) *Attorney, Agent, or Firm* — Cermak Nakajima & McGowan LLP; Tomoko Nakajima

(57) ABSTRACT

Provided a terahertz-wave detection element with high spatial resolution and suppressing a crack occurrence. A method of manufacturing the detection element capable of detecting a spatial intensity distribution of a terahertz wave includes: a step of forming an oxide layer on one main surface of a first substrate consisting of an electro-optic crystal; a step of joining the one main surface of the first substrate and a second substrate by an adhesive consisting; a step of thinning the first substrate of a joined body, to a thickness of 1-30 μm by polishing the first substrate; and a step of obtaining a large number of terahertz-wave detection elements by cutting the joined body. The oxide layer is formed such that the first substrate becomes convex to a side of the one main surface by causing a tensile stress to act on it.

5 Claims, 7 Drawing Sheets

(51) Int. Cl.
*G01J 3/02* (2006.01)
*G01N 21/3586* (2014.01)
*G01J 3/42* (2006.01)
G02F 1/03 (2006.01)

(56) References Cited

U.S. PATENT DOCUMENTS

| | | |
|---|---|---|
| 7,372,621 B2 | 5/2008 | Yoshino et al. |
| 2007/0237481 A1 | 10/2007 | Yoshino et al. |

FOREIGN PATENT DOCUMENTS

| | | |
|---|---|---|
| JP | 2003-270598 A | 9/2003 |
| JP | 2007-256324 A | 10/2007 |
| JP | 2010-156674 A | 7/2010 |

OTHER PUBLICATIONS

Written Opinion for PCT Patent App. No. PCT/JP2013/075274 (Oct. 15, 2013).
Extended European Search Report for European Patent App. No. 13838418.9 (Apr. 14, 2016).

F I G . 1
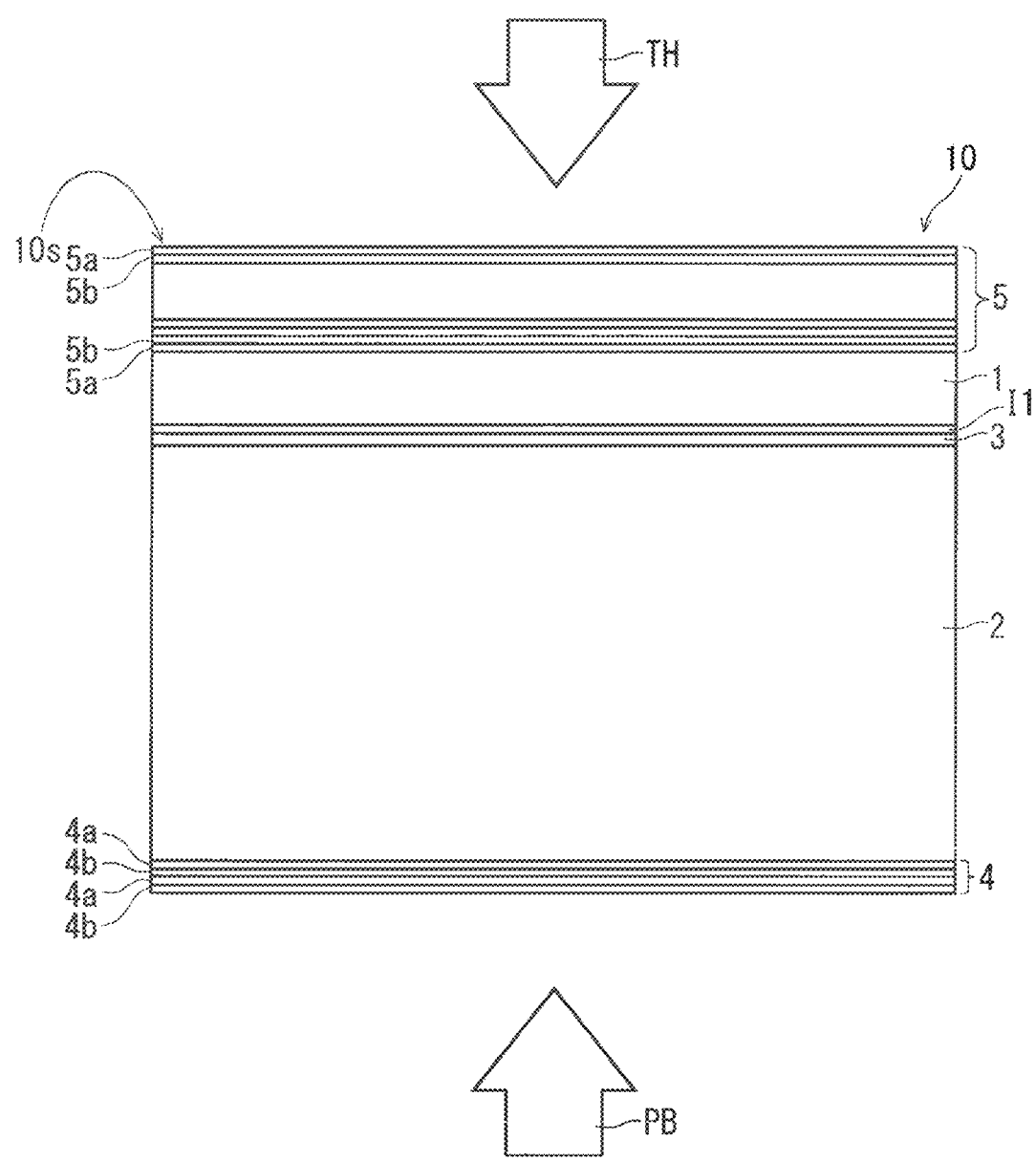

F I G . 2
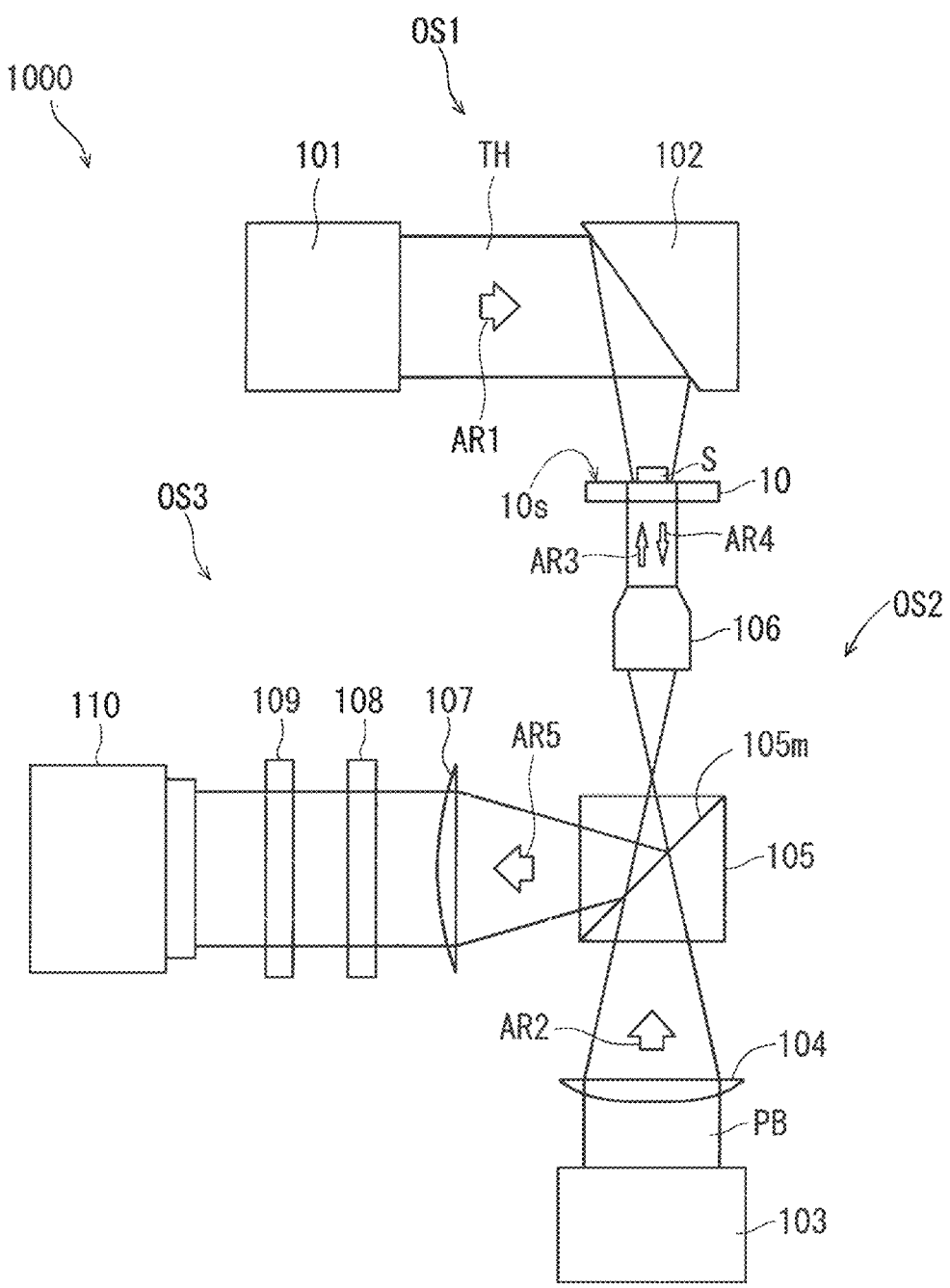

F I G . 3
S1:PREPARE MOTHER SUBSTRATES
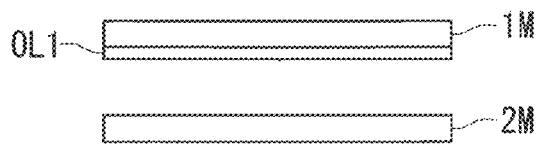
↓ S2:RESIN JOINING
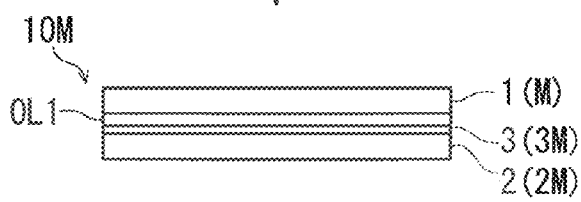
↓ S3:POLISH ELECTRO-OPTIC CRYSTAL LAYER
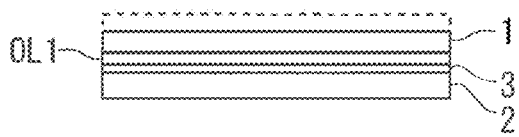
↓ S4:FORM TOTAL REFLECTION LAYER
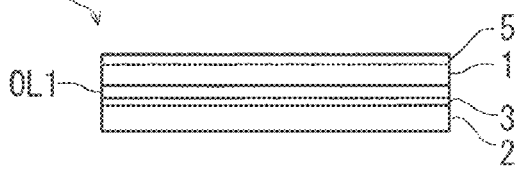
↓ S5:FORM REFLECTION PREVENTION LAYER
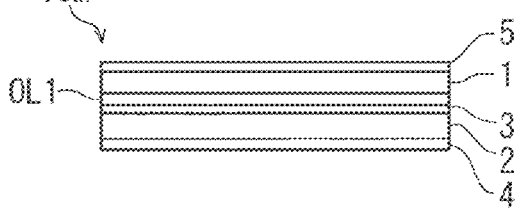
↓ S6:CUT INTO INDIVIDUAL ELEMENTS
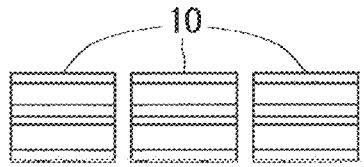

F I G. 4 A
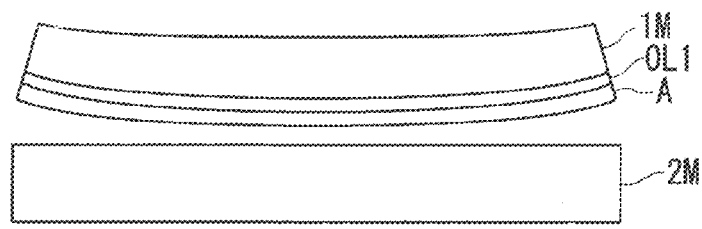
F I G. 4 B
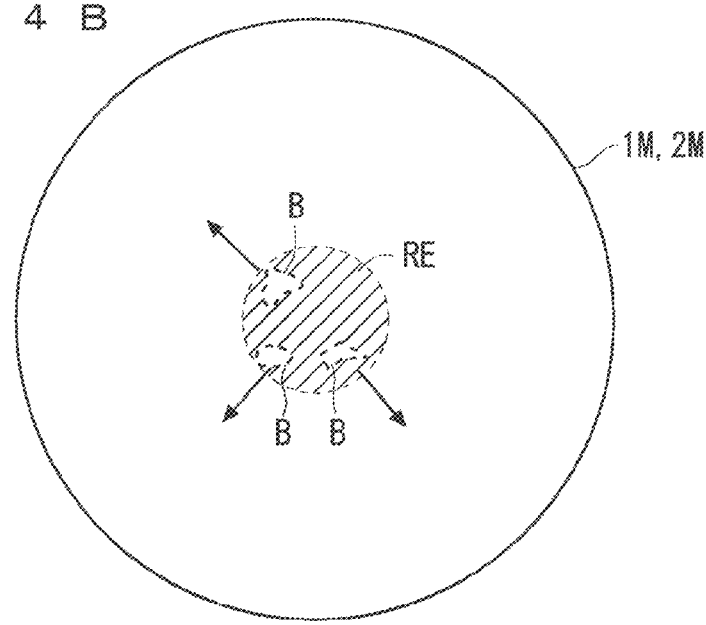
F I G. 4 C
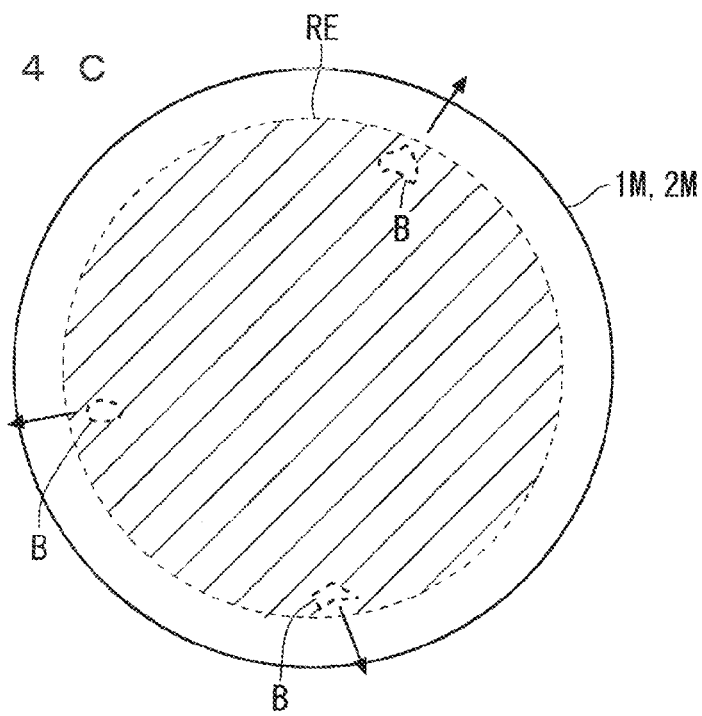

F I G . 5
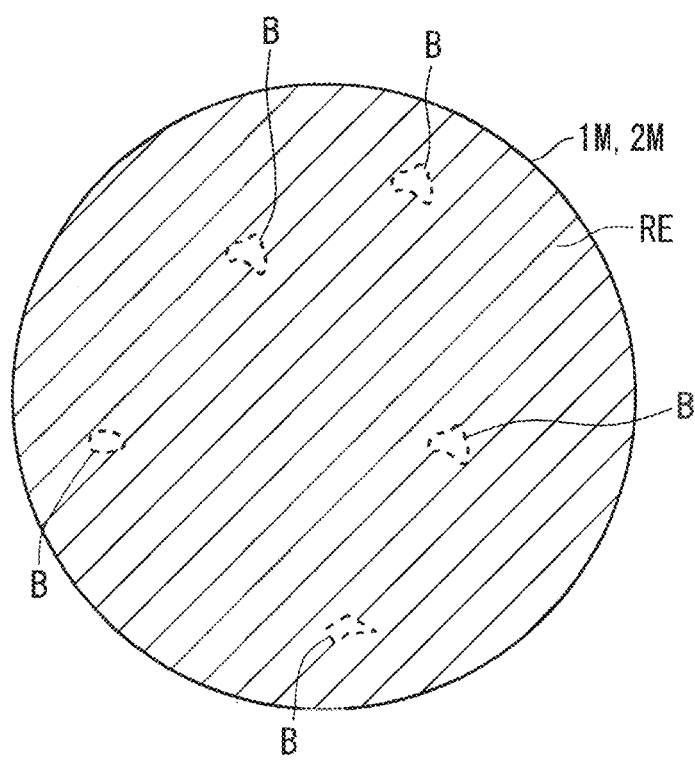

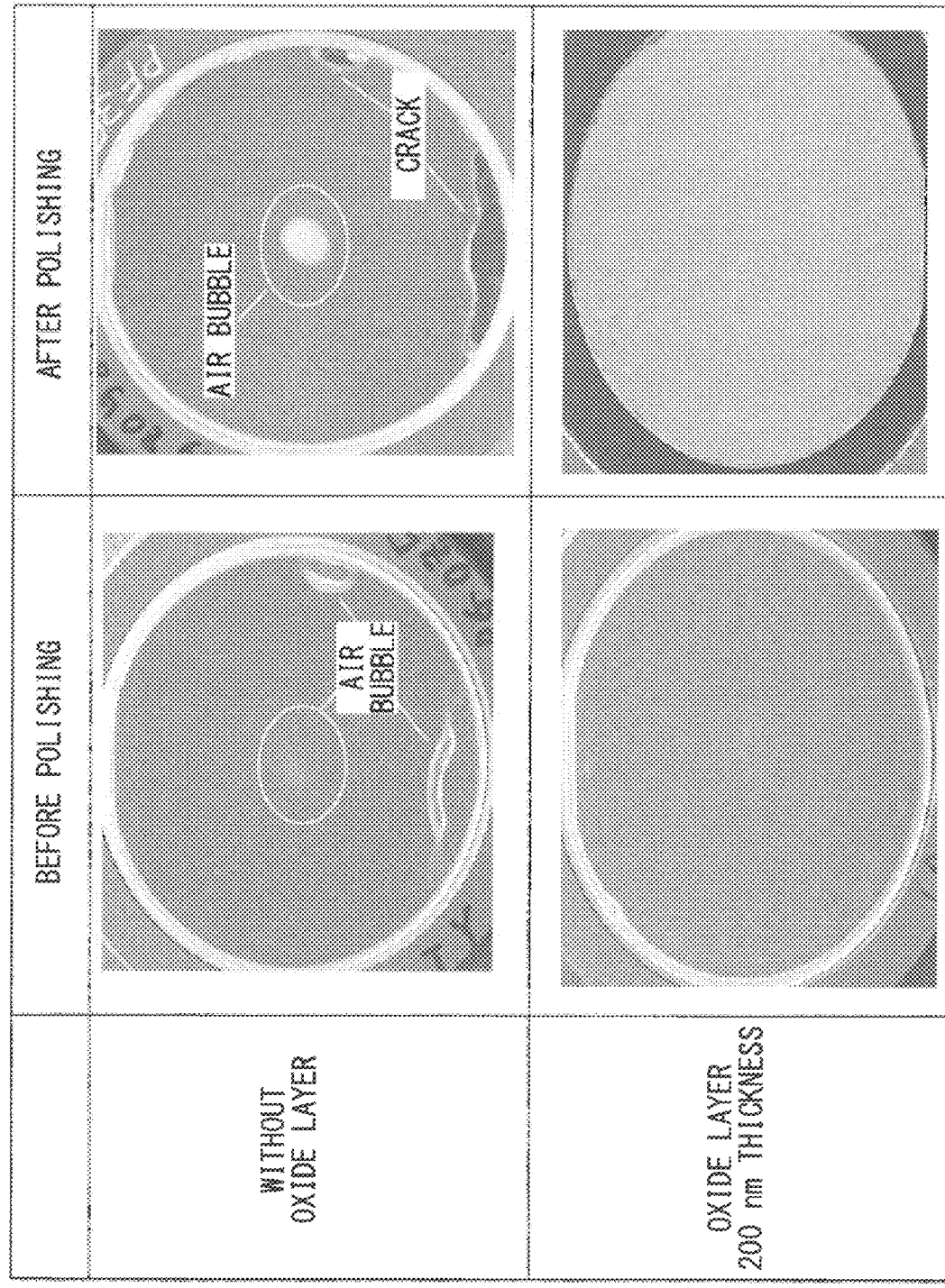

TERAHERTZ-WAVE DETECTION ELEMENT, MANUFACTURING METHOD THEREFOR, AND OBSERVATION APPARATUS

TECHNICAL FIELD

The present invention relates to an element used for detecting a terahertz wave by utilizing an electro-optic effect, and particularly relates to a terahertz-wave detection element used in an observation apparatus utilizing the terahertz wave.

BACKGROUND ART

The terahertz wave is generally an electromagnetic wave of a frequency from 0.1 THz to 30 THz. The terahertz wave is expected to be developed from the basic science field such as physical property, electron spectroscopy, life science, chemistry, pharmaceutical science, and the like to the application field such as atmospheric environmental measurement, security, material inspection, food inspection, communication, and the like.

For example, there have been expected applications of the terahertz wave to an image diagnosis apparatus which non-destructively diagnoses (inspects) an object in order to utilize characteristics that photon energy is small and the frequency is higher than that of a microwave and a millimeter wave. Particularly, because its wavelength range includes an absorption wavelength peculiar to a constitutive substance of a biological cell, there have been expected applications of the terahertz wave to an apparatus that can inspect and observe the biological cell in real time. Conventionally, inspection and observation of the biological cell cannot be performed without dyeing because of using a pigment. Therefore, it has taken time and labor for the inspection and the observation. For example, there is already publicly known an apparatus that can observe by utilizing the terahertz wave, a cell sample which it is difficult to observe by visible light (refer to Patent Document 1, for example).

In the apparatus disclosed in Patent Document 1, an electro-optic single crystal is used as a detection element of the terahertz wave. Specifically, there is used a characteristic of an electro-optic single crystal that a refractive index changes in accordance with the intensity of an incident terahertz wave. The change in the refractive index can be detected as a change in a phase, polarization, and intensity (a light quantity) of light, when the light such as infrared light (referred to as detection light, probe light, and the like) is irradiated in superposition to an electro-optic single crystal to which the terahertz wave is being irradiated. In the apparatus disclosed in Patent Document 1, a terahertz wave having a spatial distribution generated in the intensity (spatially modulated intensity) due to transmission through a specimen is incident to the electro-optic crystal. A spatial distribution of a refractive index change generated in the electro-optic single crystal in accordance with the intensity distribution is read as a light quantity distribution of near-infrared light. By this arrangement, the specimen can be observed.

In an observation apparatus that performs observation based on this principle, in order to obtain high spatial resolution, it is required to thin the electro-optic crystal as much as possible such that the terahertz wave transmitted through the specimen does not spread due to the influence of diffraction. In Patent Document 1, there is also disclosed a terahertz-wave detection element in which the electro-optic crystal is supported by a reinforcing member, by having the electro-optic crystal itself formed extremely thin.

On the other hand, there is also already publicly known a terahertz electromagnetic wave detector that uses a ZnTe crystal of a thickness equal to or larger than 5 μm and equal to or smaller than 100 μm as the electro-optic crystal, in order to reduce the influence of a multiple reflection and expand a measurable terahertz band (refer to Patent Document 2, for example). According to a technique disclosed in Patent Document 2, a ZnTe crystal is also used in a supporting substrate that supports the electro-optic crystal, and both crystals are joined together by thermocompression.

Further, there is also already publicly known an adhered body having a lithium niobate single crystal or a lithium tantalate single crystal as the electro-optic crystal equal to or larger than 0.1 μm and equal to or smaller than 10 μm and having a supporting substrate adhered thereto by a resin having a fluorene skeleton (refer to Patent Document 3, for example).

As described above, in order to obtain high spatial resolution in the observation apparatus using the terahertz wave, it is required to thin the electro-optic crystal used for detection. In order to realize this, a terahertz-wave detection element is usually manufactured by thinning an electro-optic crystal after the electro-optic crystal and a supporting substrate are joined by thermocompression disclosed in Patent Document 2 or by a method of resin adhesion disclosed in Patent Document 3.

In describing in more in detail, the terahertz-wave detection element is generally formed in a relatively small size of about a few mm square to a few cm square in a planar view. Therefore, as described above, in order to improve manufacturing efficiency and secure accuracy of thinning the layer, the terahertz-wave detection element having the thin-layer electro-optic crystal is usually obtained by performing what is called a multi-piece forming as follows. The electro-optic crystal and the supporting substrate are respectively prepared as large-size mother substrates. Both mother substrates are joined together to obtain a joined body. The electro-optic crystal is thinned by mechanical polishing and the like. Finally, the joined body is cut into elements (chips) of desired sizes. Further, a film formation processing (a coating processing) in the case of providing a total reflection film and a reflection prevention film on the front and back surfaces of the detection element in order to improve detection efficiency is also usually performed to the mother substrates.

Moreover, in order to realize high spatial resolution, the terahertz-wave detection element needs to have excellent flatness and excellent parallelism. That is, it is necessary that the terahertz-wave detection element has small warping and small surface unevenness. When the flatness and parallelism of the terahertz-wave detection element used in the observation apparatus are poor, there occurs a phenomenon that an observation image is degraded or blurred, and satisfactory observation cannot be performed.

In the case of performing multiple piece forming as described above, a joined body of mother substrates before cutting needs to have excellent flatness and parallelism. For example, in order to obtain spatial resolution at least equal to or smaller than 20 μm, flatness equal to or smaller than 25 μm and parallelism equal to or smaller than 3 μm are necessary in the state after thinning the mother substrate of the electro-optic crystal, in terms of conversion to the joined body of a 4-inch diameter mother substrate. In order to realize such flatness and parallelism in the joined body, the mother substrate of the supporting substrate needs to satisfy these conditions of the flatness and parallelism.

However, conventionally, when flatness is high, there has been a problem in that an air bubble is included in the joined part at the time of joining the two mother substrates by resin adhesion.

When an air bubble exists in the joined part, in the process of thinning the mother substrate of the electro-optic crystal by polishing, the mother substrate is broken at a portion of the air bubble in some cases, and broken pieces scatter to good portions having no air bubble and form scratches. In this case, if the scratches are deep to such an extent that they cannot be removed by subsequent polishing, the total joined body becomes a defective product.

Further, when observation is performed by using a terahertz-wave detection element in which the air bubble exists on a joined surface between the electro-optic crystal and the supporting substrate, there arises a problem in that detection light is scattered or is irregularly reflected at the air bubble portion, and a change in the refractive index generated in the terahertz-wave electro-optic crystal cannot be detected in a high S/N ratio, and high spatial resolution cannot be obtained.

PRIOR ART DOCUMENTS

Patent Documents

Patent Document 1: Japanese Patent Application Laid-Open Number 2010-156674
Patent Document 2: Japanese Patent Application Laid-Open Number 2003-270598
Patent Document 3: Japanese Patent Application Laid-Open Number 2002-337274

SUMMARY OF INVENTION

The present invention has been made in view of the above problems, and an object of the present invention is to provide in a stable quality a terahertz-wave detection element having no air bubble in a joined part and in high spatial resolution.

In order to solve the problems, according to a first aspect of the present invention, there is provided a method of manufacturing a terahertz-wave detection element capable of detecting a spatial intensity distribution that an incident terahertz wave has. The method includes: an oxide formation step of forming an oxide layer on one main surface of a first substrate consisting of an electro-optic crystal in which a refractive index at an incident position of a terahertz wave changes in accordance with incident intensity of the terahertz wave at the incident position; a joining step of joining the one main surface of the first substrate and a second substrate that supports the electro-optic crystal layer, by an adhesive consisting of a thermosetting resin; a polishing step of thinning the first substrate of a joined body obtained by the joining step, to a thickness equal to or larger than 1 μm and equal to or smaller than 30 μm by polishing the first substrate; and a segmentation step of obtaining a large number of terahertz-wave detection elements by cutting the joined body into pieces of a predetermined element size. In the oxide formation step, the oxide layer is formed such that the first substrate becomes convex to a side of the one main surface by causing a tensile stress to act on the first substrate.

According to a second aspect of the present invention, the method of manufacturing a terahertz-wave detection element according to the first aspect is for forming the oxide layer in a thickness equal to or larger than 10 nm and equal to or smaller than 1 μm in the oxide formation step.

According to a third aspect of the present invention, the method of manufacturing the terahertz-wave detection element according to the first or second aspect further includes: a total-reflection layer formation step of forming a total reflection layer consisting of a first dielectric multilayer film on a surface of the electro-optic crystal of the joined body after the polishing step; and a reflection-prevention layer formation step of forming a reflection prevention layer consisting of a second dielectric multilayer film on a surface of the second substrate of the joined body after the polishing step.

According to a fourth aspect of the present invention, there is provided a terahertz-wave detection element capable of detecting a spatial intensity distribution that an incident terahertz wave has. The terahertz-wave detection element includes: an electro-optic crystal layer consisting of an electro-optic crystal in which a refractive index at an incident position of the terahertz wave changes in accordance with incident intensity of the terahertz wave at the incident position; a supporting substrate that supports the electro-optic crystal layer; and a resin layer for joining the electro-optic crystal layer and the supporting substrate together. The terahertz-wave detection element is configured to detect a spatial-characteristics distribution which is generated in probe light irradiated to the electro-optic crystal layer in superposition with the terahertz wave and which corresponds to a spatial distribution of a refractive index generated in the electro-optic crystal layer by incidence of the terahertz wave, thereby to detect the spatial intensity distribution of the incident terahertz wave. An interposition layer consisting of an oxide and for causing a tensile stress to act on the electro-optic crystal layer is provided between the resin layer and the electro-optic crystal layer.

According to a fifth aspect of the present invention, the terahertz-wave detection element according to the fourth aspect further includes a total reflection layer consisting of a first dielectric multilayer film, formed on a surface of the electro-optic crystal, and a reflection prevention layer consisting of a second dielectric multilayer film, formed on a surface of the supporting substrate.

According to a sixth aspect of the present invention, there is provided an observation apparatus including a terahertz-wave detection element capable of detecting a spatial intensity distribution that an incident terahertz wave has. The terahertz-wave detection element includes: an electro-optic crystal layer consisting of an electro-optic crystal in which a refractive index at an incident position of said terahertz wave changes in accordance with incident intensity of said terahertz wave at said incident position, a supporting substrate that supports said electro-optic crystal layer, and a resin layer for joining said electro-optic crystal layer and said supporting substrate together. The observation apparatus further includes: a terahertz-wave irradiation optical system that irradiates the terahertz wave toward the mounting surface on which the specimen is mounted; a probe-light irradiation optical system that irradiates the probe light from a side of the supporting substrate to the electro-optic crystal layer; and an observation optical system that observes an image of the probe light having a spatial-characteristics distribution emitted from the electro-optic crystal layer in which a spatial distribution of the refractive index is generated by incidence of the terahertz wave. The terahertz-wave detection element is configured to detect a spatial-characteristics distribution which is generated in probe light irradiated to the electro-optic crystal layer in superposition with the terahertz wave and which corresponds to a spatial distribution of a refractive index generated in the electro-optic crystal layer by incidence of the terahertz wave, thereby to detect the spatial intensity distribution of the incident terahertz wave. An interposition layer consisting of an oxide and for causing a tensile stress to act on the electro-optic crystal layer is provided between the resin layer and the electro-optic crystal layer.

According to the first to fifth aspects of the present invention, there can be realized a terahertz-wave detection element with crack free and high spatial resolution.

According to the sixth aspect of the present invention, it is possible to realize an observation apparatus capable of observing a biological sample in high spatial resolution and in real time.

BRIEF DESCRIPTION OF DRAWINGS

FIG. 1 is a schematic sectional view showing a configuration of a terahertz-wave detection element 10.

FIG. 2 is a view schematically showing a configuration of an observation apparatus 1000 built in with the terahertz-wave detection element 10.

FIG. 3 is a view schematically showing an outline of a flow of manufacturing the terahertz-wave detection element 10.

FIGS. 4A to 4C are views expressing in detail a state of sticking a first mother substrate 1M and a second mother substrate 2M together by an adhesive.

FIG. 5 is a view expressing a state of sticking the first mother substrate 1M and the second mother substrate 2M together by an adhesive without providing an oxide layer OL1.

FIG. 7 is a view showing a photograph of appearance before and after polishing an electro-optic crystal layer 1 of a joined body 10M in which a thickness of the oxide layer OL1 is 0 nm and 200 nm

DESCRIPTION OF EMBODIMENTS

<Configuration of Terahertz-wave Detection Element>

Figure 6:
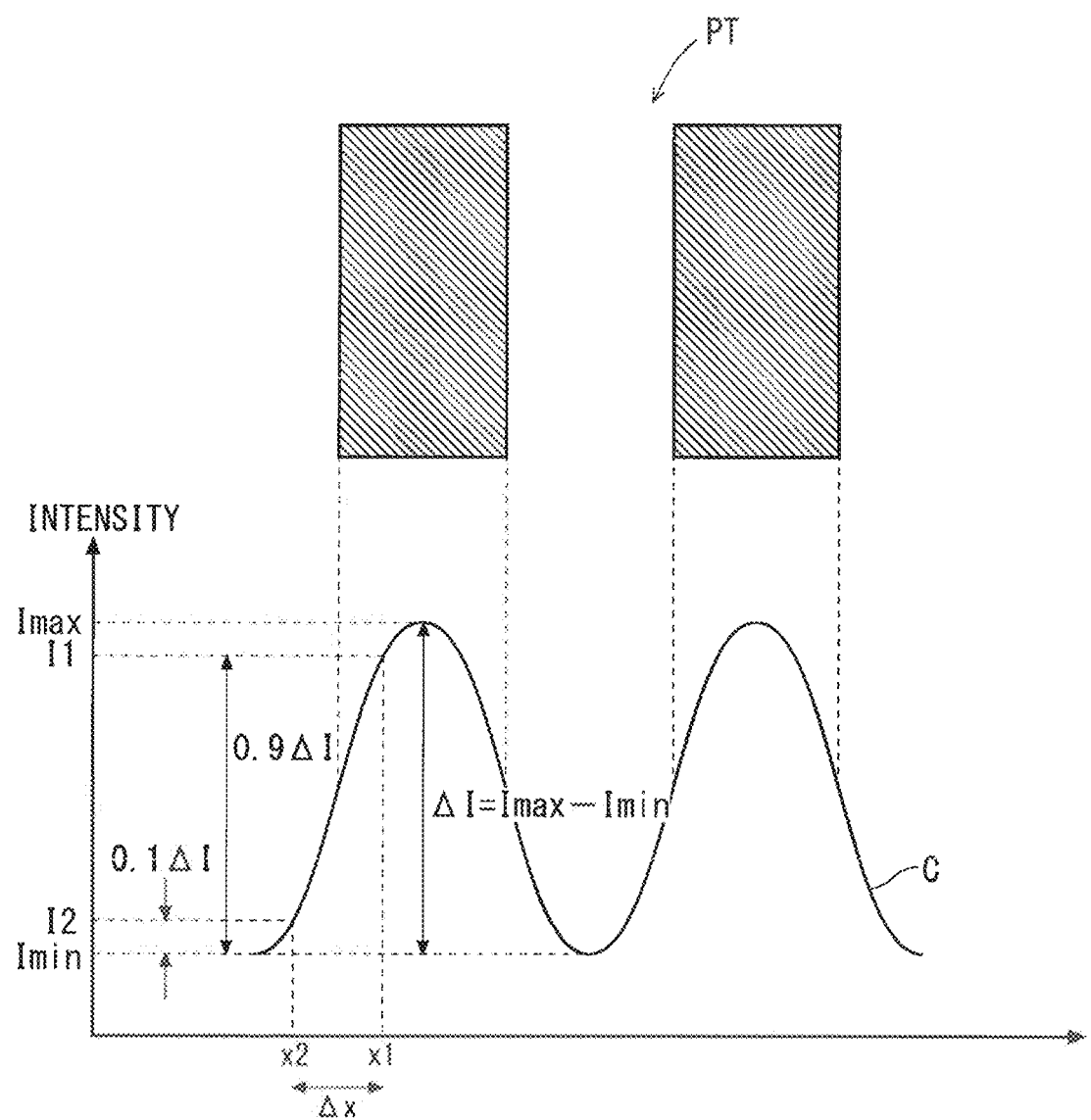
FIG. 6 is a view for explaining a method of specifying spatial resolution by using a spatial-resolution evaluation pattern PT.

FIG. 1 is a schematic sectional view showing a configuration of a terahertz-wave detection element 10 according to the present embodiment. FIG. 2 is a view schematically showing a configuration of an observation apparatus 1000 built in with the terahertz-wave detection element 10. A large and small relationship of a thickness of each layer in FIG. 1 does not reflect actual thicknesses.

As shown in FIG. 1, the terahertz-wave detection element 10 according to the present embodiment mainly includes an electro-optic crystal layer 1, a supporting substrate 2, and a resin layer 3 as a joining layer between the electro-optic crystal layer 1 and the supporting substrate 2. However, more specifically, an interposition layer I1 exists in a joined part of the electro-optic crystal layer 1.

The terahertz-wave detection element 10 is mainly used in the observation apparatus 1000 that performs inspection and observation of a biological cell, as shown in FIG. 2. In the observation apparatus 1000, a terahertz wave TH and a probe light PB are irradiated in superposition to the terahertz-wave detection element 10, in a state that a specimen S (FIG. 2) such as a biological cell is mounted on a mounting surface 10s of the terahertz-wave detection element 10. That is, in the observation apparatus 1000, the terahertz-wave detection element 10 also plays a role of a stage of the specimen S. The terahertz-wave detection element 10 may have a plane surface sufficient enough to hold the specimen S, and representatively, has a size of about a few mm square in a planar view. Further, details of the observation apparatus 1000 and observation of the specimen S using the observation apparatus 1000 will be described later.

For an electro-optic crystal that forms the electro-optic crystal layer 1, there can be exemplified a lithium niobate (LN) crystal, a lithium tantalate (LT) crystal, a ZnTe crystal, a GaAs crystal, a GaP crystal, a KTP ($KTiOPO_4$) crystal, and a DAST (4-dimethylamino-N-methyl-4-stilbazolium tosylate) crystal, for example. Among the above, LN and LT may be in a stoichiometry composition, or may be doped with MgO and the like in advance for the purpose of reducing an optical damage. Further, in the case of using LN and LT, it is preferable that an x-cut plate or a y-cut plate having a z axis existing in an in-plane direction is used so that r33 of a large electro-optic effect can be utilized as an electro-optic constant.

A thickness of the electro-optic crystal layer 1 needs to be equal to or smaller than 30 μm. When a thickness of the electro-optic crystal layer 1 is set larger than 30 μm, a crack can occur in the electro-optic crystal layer 1 in a manufacturing process of the terahertz-wave detection element 10, and therefore, this size is not preferable. A thickness of the electro-optic crystal layer 1 is preferably equal to or smaller than 10 μm. When a thickness of the electro-optic crystal layer 1 is equal to or smaller than 10 μm, it is possible to set the spatial resolution to equal to or smaller than 20 μm when the terahertz-wave detection element 10 is used in the observation apparatus 1000. When the spatial resolution is equal to or smaller than 20 μm, the biological sample can be satisfactorily observed.

The smaller a thickness of the electro-optic crystal layer 1 is, the higher the spatial resolution becomes. However, from the viewpoint of processing accuracy and from the viewpoint of detection accuracy of the probe light PB, it is preferable that the electro-optic crystal layer 1 has a thickness equal to or larger than 1 μm.

The interposition layer I1 is formed to improve joining property with the supporting substrate 2 in the process of manufacturing the terahertz-wave detection element 10. The interposition layer I1 consists of an oxide for causing a tensile stress to act on the electro-optic crystal layer 1. How to join the electro-optic crystal layer 1 and the supporting substrate 2 and a detail of the interposition layer I1 will be described later.

The supporting substrate 2 is a substrate that supports the electro-optic crystal layer 1 having a small thickness as described above. The supporting substrate 2 may be configured by any of amorphous, a single crystal, and a polycrystal, but is preferably not an electro-optic crystal. In addition, it is preferable that an azimuth of the supporting substrate 2 is determined so that susceptibility to an electric field in a substrate horizontal direction is small. In view of the above points, for the supporting substrate 2, it is suitable to use a glass substrate, a quartz substrate, an alumina substrate, a magnesium oxide substrate, and the like. Regarding a thickness of the supporting substrate 2, there is no particular limit so far as a certain level of strength and handleability can be secured. However, it is suitable to use the supporting substrate 2 of a thickness of about a few hundred μm to a few mm From the viewpoint of preventing a scattering of the probe light PB, it is preferable that a surface roughness of the supporting substrate 2 is equal to or smaller than 1/5 of the wavelength of the probe light PB.

The resin layer 3 is a joining layer between the electro-optic crystal layer 1 (more strictly, at its side where the interposition layer I1 is provided) and the supporting substrate 2. The resin layer 3 is a layer consisting of an epoxy thermosetting resin. The resin layer 3 has a coefficient of thermal expansion larger than the coefficient of thermal expansion of the electro-optic crystal layer 1.

From the viewpoint of holding a joining state between the electro-optic crystal layer 1 and the supporting substrate 2, it is sufficient for the resin layer 3 to have a thickness equal to or larger than 0.1 µm. However, from the viewpoint of suppressing warping in the terahertz-wave detection element 10 and preventing the occurrence of a crack in the electro-optic crystal layer 1, it is preferable to form the resin layer 3 in a thickness equal to or smaller than 1 µm.

The electro-optic crystal layer 1, the supporting substrate 2, and the resin layer 3 that joins the electro-optic crystal layer 1 and the supporting substrate 2 described above together are basic components of the terahertz-wave detection element 10.

However, the terahertz-wave detection element 10 according to the present embodiment includes a reflection prevention layer 4 and a total reflection layer 5, for the purpose of improving observation performance when used in the observation apparatus 1000.

The reflection prevention layer 4 is formed on a surface of the supporting substrate 2 at the opposite side of the resin layer 3. The reflection prevention layer 4 is provided to prevent reflection on the surface of the supporting substrate 2, of the probe light PB incident to the terahertz-wave detection element 10 from the supporting substrate 2 side.

Specifically, the reflection prevention layer 4 is formed on the main surface of the supporting substrate 2, as a dielectric multilayer film formed by repeatedly and alternately stacking a first-unit reflection prevention layer 4a and a second-unit reflection prevention layer 4b made of dielectrics of mutually different compositions. As dielectrics that can be used to form the reflection prevention layer 4, there can be exemplified silicon oxide, tantalum oxide, titanium oxide, magnesium fluoride, zirconia, aluminum oxide, niobium oxide, and zinc sulfide. Alternatively, the reflection prevention layer 4 may be a single layer film of either of the above dielectrics.

For example, by a deposition method, it is suitable to provide the reflection prevention layer 4 in a total thickness of about 0.2 µm to 0.5 µm, by forming the first-unit reflection prevention layer 4a consisting of $Ta_2O_5$ and the second-unit reflection prevention layer 4b consisting of $SiO_2$ respectively in a thickness of several dozens of nm to a hundred and several dozens of nm. Accordingly, the reflection prevention layer 4 of reflectance equal to or lower than 0.1% can be provided.

The total reflection layer 5 is formed on the surface of the electro-optic crystal layer 1, at the opposite side of the resin layer 3. The total reflection layer 5 is provided to make a total reflection of the probe light PB incident to the terahertz-wave detection element 10 from the supporting substrate 2 side.

Specifically, the total reflection layer 5 is formed on the main surface of the electro-optic crystal layer 1, as a dielectric multilayer film formed by stacking repeatedly and alternately the first-unit total reflection layer 5a and the second-unit total reflection layer 5b consisting of dielectrics of mutually different compositions. The total reflection layer 5 has a coefficient of thermal expansion smaller than the coefficient of thermal expansion of the electro-optic crystal layer 1. In the present embodiment, the coefficient of thermal expansion of the total reflection layer 5 as a multi-layer film of the first-unit total reflection layer 5a and the second-unit total reflection layer 5b of mutually different compositions is assumed to be an effective (average) value as a layer in total. As the dielectrics that can be used to form the total reflection layer 5, there can be exemplified silicon oxide, tantalum oxide, titanium oxide, magnesium fluoride, zirconia, aluminum oxide, hafnium oxide, niobium oxide, and zinc sulfide.

For example, by a deposition method, it is suitable to provide the total reflection layer 5 in a total thickness of about a few µm, by forming the first-unit total reflection layer 5a consisting of $SiO_2$ and the second-unit total reflection layer 5b consisting of $Ta_2O_5$ respectively in a thickness of a submicron order, respectively. Accordingly, it is possible to provide the total reflection layer 5 of reflectance equal to or higher than 99% and a coefficient of thermal expansion smaller than a coefficient of thermal expansion in the z axis direction of the LN crystal.

When the terahertz-wave detection element 10 includes the reflection prevention layer 4 and the total reflection layer 5, the loss of the incident probe light PB is reduced, and therefore, the quality of an observation image in the case of using the terahertz-wave detection element 10 in the observation apparatus 1000 improves.

<Observation by Observation Apparatus>

Next, there will be described a configuration of the observation apparatus 1000, and an observation mode of the specimen S using the observation apparatus 1000. As shown in FIG. 2, the observation apparatus 1000 includes a terahertz-wave irradiation optical system OS1, a probe-light irradiation optical system OS2, and an observation optical system OS3, in addition to the terahertz-wave detection element 10 as a stage on which the specimen S is mounted.

The terahertz-wave irradiation optical system OS1 mainly includes a terahertz-wave generation source 101 and a parabolic mirror 102. The terahertz-wave generation source 101 is configured to generate a terahertz wave TH by irradiating a femtosecond titanium laser beam of a wavelength 800 µm to a terahertz-wave conversion element.

The probe-light irradiation optical system OS2 mainly includes a probe-light light source 103, a first intermediate lens 104, a non-polarization beam splitter 105, and an objective lens 106. For the probe light PB, there is used a femtosecond titanium laser beam which is the same as that used in the terahertz-wave generation source 101. Therefore, by branching the femtosecond titanium laser beam emitted from the probe-light light source 103 into two directions in the middle, one femtosecond titanium laser beam may be used as the probe light PB, and the other femtosecond titanium laser beam may be utilized to generate the terahertz wave TH in the terahertz-wave generation source 101. In this case, the probe-light light source 103 may be configured as a system capable of measuring by what is called a THz-TDS (Terahertz Time Domain Spectroscopy) method, where the terahertz light is detected by sampling with a light delay unit.

The observation optical system OS3 mainly includes a second intermediate lens 107, a 1/4 wavelength plate 108, a polarizer 109, and an imaging device 110 consisting of a CCD, for example.

In the observation apparatus 1000 having the above configuration, in the state that the specimen S is mounted on the mounting surface 10s of the terahertz-wave detection element 10, the terahertz wave TH emitted from the terahertz-wave generation source 101 as shown by an arrow AR101, and reflected and converged by the parabolic mirror 102, is irradiated to the specimen S. As described above, because the terahertz-wave detection element 10 includes the total reflection layer 5, actually, the surface of the total reflection layer 5 becomes the mounting surface 10s.

The terahertz wave TH irradiated to the specimen S is absorbed in accordance with a spatial distribution (a two-dimensional distribution) of a cellular component, a thickness, and the like in the specimen S, and intensity of the terahertz wave TH is spatially (two-dimensionally) modulated. Then, the modulated terahertz wave TH is incident to the electro-optic crystal layer 1 of the terahertz-wave detection element 10. After that, in the electro-optic crystal layer 1, there is generated by a Pockels effect a distribution in levels of a refractive index change by a double refraction, in accordance with an intensity distribution generated in the incident terahertz wave TH. In other words, the refractive index at the incident position of the terahertz wave TH varies in accordance with incident intensity of the terahertz wave TH at its incident position. As a result, the distribution of the refractive index change (the distribution of the refractive index eventually) reflects spatial information of the specimen S.

On the other hand, in the observation apparatus 1000, the probe light PB emitted from the probe-light source 103 as a parallel light is converted into a non-parallel light by the first intermediate lens 104. After that, as shown by an arrow AR2 and an arrow AR3, the non-parallel light passes through the non-polarization beam splitter 105 and the objective lens 106, and is incident as a parallel light from the supporting substrate 2 side (from the reflection prevention layer 4 side) to the terahertz-wave detection element 10. For the probe light PB, there is used the probe light PB of a wavelength band 800 nm Since the terahertz-wave detection element 10 according to the present embodiment includes the reflection prevention layer 4 on the surface of the supporting substrate 2, the probe light PB is incident to the electro-optic crystal layer 1 substantially without receiving loss.

The probe light PB incident to the electro-optic crystal layer 1 is totally reflected by the total reflection layer 5 comprised in the terahertz-wave detection element 10, while it is refracted in accordance with the refractive index distribution generated in the electro-optic crystal layer 1 according to the intensity distribution of the terahertz wave TH as described above. Then, as shown by an arrow AR4, the probe light PB is emitted toward the objective lens 106 and the non-polarization beam splitter 105. The probe light PB emitted from the terahertz-wave detection element 10 in this manner has a spatial distribution of intensity (a light quantity) reflecting the spatial distribution of the refractive index (a refractive index change).

The probe light PB emitted from the terahertz-wave detection element 10 and incident to the non-polarization beam splitter 105 is reflected by a half-mirror 105m comprised in the non-polarization beam splitter 105. Then, as shown by an arrow AR5, the probe light PB is converted into a parallel light by the second intermediate lens 107, sequentially passes through the ¼ wavelength plate 108 and the polarizer 109, and is incident to the imaging device 110.

As described above, the probe light PB incident to the imaging device 110 has the intensity distribution reflecting the refractive index distribution generated in the electro-optic crystal layer 1 in the terahertz-wave detection element 10. The refractive index distribution has been generated by the incidence to the electro-optic crystal layer 1, of the terahertz wave TH which has transmitted through the specimen S. As a result, in the observation apparatus 1000, an image formed in the imaging device 110 represents a distribution in the spatial (two-dimensional) state of the specimen S. Accordingly, in the observation apparatus 1000, the specimen S can be observed in real time by observing the image formed in the imaging device 110.

<Manufacturing Method of Terahertz-wave Detection Element>

Next, a manufacturing method of the terahertz-wave detection element 10 having the above configuration according to the present embodiment will be described in detail. FIG. 3 is a view schematically showing an outline of a flow of manufacturing the terahertz-wave detection element 10 according to the present embodiment.

As described above, the terahertz-wave detection element 10 according to the present embodiment is based on the configuration having the electro-optic crystal layer 1 and the supporting substrate 2 joined together by the resin layer 3. Because the planar size of the terahertz-wave detection element 10 is at most about a few mm square, it is difficult and inefficient to perform joining by preparing the electro-optic crystal layer 1 and the supporting substrate 2 of this planar size. Therefore, in the present embodiment, the terahertz-wave detection element 10 is manufactured by what is called a multi-piece forming First, as shown in FIG. 3, there are prepared a first mother substrate 1M and a second mother substrate 2M having sufficiently large sizes (diameters) as compared with the element size (Step S1). For example, it is suitable to prepare the first mother substrate 1M and the second mother substrate 2M of a few inch diameter. Then, the main surface at the side of the first mother substrate 1M on which the oxide layer OL1 is formed and the main surface of the second mother substrate 2M are joined together by resin adhesion, thereby to obtain the joined body 10M (Step S2).

The first mother substrate 1M is a substrate having the same composition and the same crystal state as those of the electro-optic crystal layer 1, and also having a large thickness. Concerning the thickness of the first mother substrate 1M, a value of the thickness is required to be such a degree that a certain level of strength and handleability can be secured. On the other hand, when a difference in the thickness between the first mother substrate 1M and the electro-optic crystal layer 1 finally configuring the terahertz-wave detection element 10 is too large, excessive time is required in the polishing process described later. Therefore, it is suitable to use the first mother substrate 1M of a thickness of about a few hundred μm to a few mm, for example.

The second mother substrate 2M is a substrate having the same composition, the same crystal state, and the thickness as those of the supporting substrate 2. However, for the second mother substrate 2M, it is preferable to use the second mother substrate 2M of flatness equal to or smaller than 25 μm and parallelism equal to or smaller than 3 μm, and more preferably, flatness equal to or smaller than 15 μm and parallelism equal to or smaller than 2 μm. When these requirements are satisfied, warping and unevenness in the terahertz-wave detection element 10 are suppressed, and therefore, excellent spatial resolution, equal to or smaller than 20 μm, or equal to or smaller than 10 μm, can be realized, respectively. That is, the terahertz-wave detection element 10 with excellent spatial resolution can be obtained.

Unless particularly specified, in the present description, flatness and parallelism are expressed as values converted for a substrate (or a joined body) of 4-inch diameter.

Prior to the resin adhesion, there is formed in advance by a sputtering method, the oxide layer OL1 on one main surface of the first mother substrate 1M. More specifically, the oxide layer OL1 is formed such that a tensile stress acts on the main surface and the vicinity of the main surface. For example, this can be realized by forming an oxide layer of $SiO_2$, $Ta_2O_5$, and the like in the thickness equal to or larger than 10 nm However, the oxide layer OL1 is formed equal to or smaller than 1 μm. When the thickness of the oxide layer OL1 is set larger than 1 μm, warping of the first mother substrate 1M becomes too large, and warping occurs in the joined body 10M which is obtained as a result of the joining. Further, flatness and parallelism of the joined body 10M are deteriorated. Therefore, this is not preferable. When flatness and parallelism are deteriorated, an electro-optic constant of the electro-optic crystal layer 1 is deteriorated, and satisfactory spatial resolution of equal to or smaller than 20 μm cannot be obtained in the terahertz-wave detection element 10. More preferably, the oxide layer OL1 is formed equal to or smaller than 500 nm, and further more preferably, equal to or smaller than 200 nm. In such cases, a terahertz-wave detection element with more excellent spatial resolution is realized.

The resin adhesion is performed by coating an epoxy adhesive A (refer to FIGS. 4A to 4C) on the main surface at the side of the first mother substrate 1M on which the oxide layer OL1 is formed (more strictly, on the surface of the oxide layer OL1) firstly, and then by sticking a second mother substrate 2M thereto such that their orientation flats coincide.

FIGS. 4A to AC are views expressing in detail a state of sticking the first mother substrate 1M and the second mother substrate 2M together by an adhesive. FIG. 5 is a view expressing a state of sticking the first mother substrate 1M and the second mother substrate 2M together by an adhesive without providing the oxide layer OL1, shown for the sake of comparison.

In general, in the case of joining by sticking two substrates of high flatness equal to or smaller than a few dozens of μm by an adhesive, as shown in FIG. 5, there is a problem in that air bubbles B can easily enter a stuck region RE, and the air bubbles B once entered cannot be easily removed. The air bubbles become an origin of crack generation in the joined body 10M, and become a factor of lowering the spatial resolution of the terahertz-wave detection element 10. Therefore, the air bubbles B need to be removed as much as possible in the sticking stage.

In the present embodiment, this problem is solved by forming the oxide layer OL1. Specifically, because the oxide layer OL1 has been formed, as shown in FIG. 4A, warping has occurred only slightly in the first mother substrate 1M such that the side where the oxide layer OL1 was formed has become convex due to the act of the tensile stress. In FIGS. 4A to 4C, in order to facilitate the understanding, the warping is shown exaggeratedly.

Because of existence of slight warping in the first mother substrate 1M, sticking between the first mother substrate 1M and the second mother substrate 2M proceeds from a top convex part of the first mother substrate 1M without exception. Therefore, as shown in FIG. 4B and FIG. 4C, even when the air bubbles B exist near the top convex part, as the first mother substrate 1M and the second mother substrate 2M come close with the progress of the sticking and the stuck region RE expands, the air bubbles B move toward the outer peripheral pars of the stuck region RE as shown in FIGS. 4B and 4C, and become in contact with outer air and disappear. As a result, the sticking without a remaining of the air bubbles B can be realized.

A stuck body of the first mother substrate 1M and the second mother substrate 2M stuck in the above manner is crimped by pressing. Thereafter, the resultant is left for a few hours in the atmosphere of 200° C. to harden the adhesive to form an adhesion layer 3M, so that the joined body 10M is obtained.

After performing the process described later, the joined body 10M is finally cut into a large number of terahertz-wave detection elements 10. Then, portions originated from the first mother substrate 1M, the second mother substrate 2M, and the adhesion layer 3M respectively become the electro-optic crystal layer 1, the supporting substrate 2, and the resin layer 3 of the terahertz-wave detection element 10. For convenience sake, after the joined body 10M has been obtained, the first mother substrate 1M will be simply referred to as the electro-optic crystal layer 1, the second mother substrate 2M will be simply referred to as the supporting substrate 2, and the adhesion layer 3M will be simply referred to as the resin layer 3.

Next, the electro-optic crystal layer 1 of the obtained joined body 10M is polished by a publicly known sheet processing method, until the electro-optic crystal layer 1 has a thickness equal to the preferable thickness of the electro-optic crystal layer 1 in the above-described element state (Step S3).

After ending the polishing, an dielectric multilayer film serving as the total reflection layer 5 is formed on the polished electro-optic crystal layer 1 by a deposition method (Step S4). Next, on the supporting substrate 2, a dielectric multilayer film serving as the reflection prevention layer 4 is formed by the deposition method (Step S5). These dielectric multilayer films will be also referred to as the total reflection layer 5 and the reflection prevention layer 4, respectively, for convenience sake.

Finally, the joined body 10M formed up to the reflection prevention layer 4 is cut into predetermined element sizes on the surface along a joining direction by a publicly known method such as dicing to have a desired planar size. As a result, a large number of the terahertz-wave detection element 10 are obtained (step S6). In this case, the oxide layer OL1 becomes the interposition layer I1 in each terahertz-wave detection element 10. Because the air bubbles as the factor of lowering the spatial resolution do not exist, the obtained terahertz-wave detection element 10 has excellent spatial resolution.

As described above, according to the present embodiment, in the case of manufacturing the terahertz-wave detection element by a method of multiple piece forming, at the time of sticking together a first mother substrate consisting of the electro-optic crystal and the supporting substrate by an adhesive, by making the first mother substrate a slight convex shape with the formation of an oxide layer on the first mother substrate in advance, the first mother substrate and a second mother substrate can be stuck together without mixing air bubbles into the stuck portion. Accordingly, it is possible to stably obtain a terahertz-wave detection element with crack free and excellent spatial resolution, without existence of air bubbles between the electro-optic crystal layer and the supporting substrate.

By applying the terahertz-wave detection element to the observation apparatus, the observation apparatus capable of observing a biological sample in high spatial resolution and in real time can be realized.

<Modification>

In the above embodiment, by forming the oxide layer OL1 on the first mother substrate 1M, the terahertz-wave detection element without existence of air bubbles between the electro-optic crystal layer and the supporting substrate is realized. However, the manner of excluding the air bubbles by forming the oxide layer is not limited to this. For example, in place of the first mother substrate 1M, by forming the oxide layer on the main surface of the second mother substrate 2M, slight warping may be given to the second mother substrate 2M, and then the first mother substrate 1M and the second mother substrate 2M may be stuck together. Alternatively, the oxide layer may be formed on both the first mother substrate 1M and the second mother substrate 2M.

EXAMPLE

In the example, the joined body 10M was manufactured under seven manufacturing conditions by changing the thickness of the oxide layer OL1 to 7 levels including a case of non-forming, and presence or absence of a trouble such as the mixing of air bubbles and the occurrence of a crack were evaluated. Under each manufacturing condition, samples of five wafers were manufactured.

Specifically, in each manufacturing condition, first, for the first mother substrate 1M, there was prepared an MgO 5 mol % doped x-cut plate LN single crystal substrate in a 4-inch diameter and in a 500 μm thickness. For the second mother substrate 2M, there was prepared a TEMPAX glass in a 4-inch diameter and in a 500 μm thickness.

Flatness of the second mother substrate 2M was within 3 μm as a result of measurement by a Fujinon interferometer. Parallelism was within 1 μm as a result of measurement by a micrometer.

Next, on one main surface of the first mother substrate 1M, there was formed an $SiO_2$ layer as the oxide layer OL1 by a sputtering method. In this case, the thickness of the oxide layer OL1 was differentiated into six levels of 5 nm, 10 nm, 200 nm, 500 nm, 1000 nm, and 1100 nm. Further, the first mother substrate 1M on which the oxide layer OL1 was not formed (a thickness is 0 nm) was also prepared.

In all cases, after an epoxy adhesive is coated on a surface of the first mother substrate 1M and the second mother substrate 2M was stuck thereto such that their orientation flats coincided, they were crimped by pressing. Next, the press contacted resultant was left for one hour in the atmosphere of 200° C. to harden the adhesive to form an adhesion layer 3M (a coefficient of thermal expansion: 40 ppm/° C.), so that the joined body 10M was obtained. In this case, based on a result of preliminary experiments conducted in advance for specifying a relationship between a coating quantity of an epoxy adhesive, a pressing pressure, and a thickness of the adhesion layer 3M, the coating quantity of the epoxy adhesive and the pressing pressure at the time of pressing were adjusted such that the thickness of the adhesion layer 3M became 0.3 μm.

For the joined body 10M at this time point, appearance was observed visually and by using a microscope.

Next, the electro-optic crystal layer 1 constituting the joined body 10M was polished by a publicly known sheet processing method until its thickness of became 3 μm. The results of the measurement of flatness and parallelism of the polished electro-optic crystal layer 1 were within 5 μm and 0.5 μm, respectively.

For the polished joined body 10M, appearance was also observed visually and by using a microscope.

Thereafter, on the main surface of the electro-optic crystal layer 1 of each joined body 10M, by the deposition method, an $SiO_2$ layer as the first-unit total reflection layer 5a and a $Ta_2O_5$ layer as the second-unit total reflection layer 5b were alternately formed such that 25 layers were formed in total. Accordingly, the total reflection layer 5 as the dielectric multilayer film (a coefficient of thermal expansion: 4 ppm/° C.) was obtained. A total thickness of the total reflection layer 5 was set to 3 μm, and thicknesses of the $SiO_2$ layer and the $Ta_2O_5$ layer were 137 μm and 97 μm, respectively. As a result of evaluating the reflection characteristic, reflectance around 800 μm was equal to or higher than 99% in the range of 200 μm Further, on the main surface of the supporting substrate 2 of each joined body 10M, by the deposition method, a $Ta_2O_5$ layer as the first-unit reflection prevention layer 4a and an $SiO_2$ layer as the second-unit reflection prevention layer 4b were alternately formed by 4 layers in total. As a result, the reflection prevention layer 4 as the dielectric multilayer film was obtained. More specifically, the reflection prevention layer 4 in a total thickness of 0.3 μm was formed by sequentially forming a $Ta_2O_5$ layer in a thickness 31 nm, an $SiO_2$ layer in a thickness 40 nm, a $Ta_2O_5$ layer in a thickness 93 nm, and an $SiO_2$ layer in a thickness 125 nm from a near side of the supporting substrate 2.

Next, the terahertz-wave detection element 10 was manufactured from the joined body 10M in which up to the formation of the reflection prevention layer 4 was performed. Spatial resolution was evaluated by using the observation apparatus 1000.

FIG. 6 is a view for explaining a method of specifying spatial resolution by using the spatial-resolution evaluation pattern PT employed in the present embodiment. The spatial-resolution evaluation pattern is a line and space pattern that has a plurality of line patterns of an equal width arranged in one direction in the same interval (space) as the width of the line pattern.

In the case of specifying the spatial resolution by using the spatial-resolution evaluation pattern PT, first, there is arranged in the observation apparatus 1000 the terahertz-wave detection element 10 in which a plurality of spatial-resolution evaluation patterns PT of different lines and spaces (line widths and line intervals) are formed on the main surface at the electro-optic crystal layer 1 side. Then, the spatial-resolution evaluation pattern PT is observed.

In an intensity curve line C in the line pattern arrangement direction obtained from each spatial-resolution evaluation pattern PT, a difference value between maximum intensity Imax and minimum intensity Imin is defined as ΔI. Then, there is obtained a distance Ax between a position x1 of I1=Imin+0.9ΔI (=Imax−0.1 ΔI) and a position x2 of I2=Imin+0.1 ΔI (=Imax−0.9 ΔI). Then, a minimum value of Ax obtained from each spatial-resolution evaluation pattern PT is prescribed as the spatial resolution of the terahertz-wave detection element 10.

In the case of the present example, for each of the seven kinds of the joined body 10M, on the main surface at the electro-optic crystal layer 1 side of the sample in which air bubbles did not exist, four levels of spatial-resolution evaluation patterns PT (refer to FIG. 5) of four different lines and spaces (line widths and line intervals) 10 μm, 20 μm, 30 μm and 40 μm were formed by deposition using gold. Then, the joined body 10M was cut into 5 mm square sizes by dicing, thereby to obtain the terahertz-wave detection element 10 having such patterns. Then, spatial resolution was calculated for the terahertz-wave detection element 10.

Table 1 shows values of an air-bubbles mixing rate in the joined body 10M before the electro-optic crystal layer 1 was polished, and spatial resolution of the terahertz-wave detection element 10 manufactured from each joined body 10M. The air-bubbles mixing rate is a value expressing a ratio of samples in which air bubbles existed out of samples of the same thickness of the oxide layer OL1.

TABLE 1

| No. | Oxide layer thickness (nm) | Air-bubbles mixing rate (%) | Spatial resolution (μm) |
|---|---|---|---|
| 1 | 0 | 30 | 30 |
| 2 | 5 | 30 | 30 |
| 3 | 10 | 0 | 5 |
| 4 | 200 | 0 | 5 |
| 5 | 500 | 0 | 7 |
| 6 | 1000 | 4 | 15 |
| 7 | 1100 | 5 | 25 |

As shown in Table 1, in the samples No. 3, 4, 5, and 6 in which the thickness of the oxide layer OL1 was set equal to or larger than 10 nm and equal to or smaller than 1000 nm, satisfactory spatial resolution equal to or smaller than 20 nm was obtained. In the samples in which the thickness of the oxide layer OL1 was set equal to or larger than 10 nm and 500 nm, air bubbles were not confirmed at all. However, air bubbles existed in other samples.

FIG. 7 is a view showing a photograph of appearance before and after polishing the electro-optic crystal layer 1 of the joined body 10M in which the thickness of the oxide layer OL1 is 0 nm and 200 nm. As shown in FIG. 7, in the samples in which the oxide layer OL1 was not formed, a crack occurred by polishing at the portions where air bubbles existed before the polishing. On the other hand, in the samples in which the oxide layer OL1 was formed, air bubbles were not confirmed at all before and after the polishing.

The above result indicates that forming the oxide layer OL1 in a suitable thickness is the effective method of preventing the mixing of air bubbles into the joined body 10M, and further suppressing a crack in the joined body 10M, and improving the spatial resolution of the terahertz-wave detection element 10.

The invention claimed is:

1. A method of manufacturing a terahertz-wave detection element capable of detecting a spatial intensity distribution that an incident terahertz wave has, the method comprising:
    an oxide formation step of forming an oxide layer on one main surface of a first substrate consisting of an electro-optic crystal in which a refractive index at an incident position of a terahertz wave changes in accordance with incident intensity of said terahertz wave at the incident position;
    a joining step of joining said one main surface of said first substrate and a second substrate that supports said electro-optic crystal layer, by an adhesive consisting of a thermosetting resin;
    a polishing step of thinning said first substrate of a joined body obtained by said joining step, to a thickness from 1 μm or more to 30 μm or less by polishing said first substrate;
    a segmentation step of obtaining a large number of terahertz-wave detection elements by cutting said joined body into pieces of a predetermined element size, wherein
    in said oxide formation step, said oxide layer is formed such that said first substrate becomes convex to a side of said one main surface by causing a tensile stress to act on said first substrate;
    a total-reflection layer formation step of forming a total reflection layer consisting of a first dielectric multilayer film on a surface of said electro-optic crystal of said joined body after said polishing step; and
    a reflection-prevention layer formation step of forming a reflection prevention layer consisting of a second dielectric multilayer film on a surface of said second substrate of said joined body after said polishing step.

2. A terahertz-wave detection element capable of detecting a spatial intensity distribution that an incident terahertz wave has, the terahertz-wave detection element comprising:
    an electro-optic crystal layer consisting of an electro-optic crystal in which a refractive index at an incident position of said terahertz wave changes in accordance with incident intensity of said terahertz wave at said incident position;
    a supporting substrate that supports said electro-optic crystal layer; and
    a resin layer for joining said electro-optic crystal layer and said supporting substrate together, wherein
    said terahertz-wave detection element is configured to detect a spatial-characteristics distribution which is generated in probe light irradiated to said electro-optic crystal layer in superposition with said terahertz wave and corresponds to a spatial distribution of a refractive index generated in said electro-optic crystal layer by incidence of said terahertz wave, thereby to detect said spatial intensity distribution of said incident terahertz wave, and
    an interposition layer consisting of an oxide and for causing a tensile stress to act on the electro-optic crystal layer is provided between said resin layer and said electro-optic crystal layer.

3. The terahertz-wave detection element according to claim 2, further comprising:
    a total reflection layer consisting of a first dielectric multilayer film, formed on a surface of said electro-optic crystal, and;
    a reflection prevention layer consisting of a second dielectric multilayer film, formed on a surface of said supporting substrate.

4. An observation apparatus comprising:
    a terahertz-wave detection element capable of detecting a spatial intensity distribution that an incident terahertz wave has, the terahertz-wave detection element comprising,
        an electro-optic crystal layer consisting of an electro-optic crystal in which a refractive index at an incident position of said terahertz wave changes in accordance with incident intensity of said terahertz wave at said incident position,
        a supporting substrate that supports said electro-optic crystal layer, and
        a resin layer for joining said electro-optic crystal layer and said supporting substrate together,
    a terahertz-wave irradiation optical system that irradiates said terahertz wave toward said mounting surface on which said specimen is mounted;
    a probe-light irradiation optical system that irradiates said probe light from a side of said supporting substrate to said electro-optic crystal layer; and
    an observation optical system that observes an image of said probe light having a spatial-characteristics distribution emitted from said electro-optic crystal layer in which a spatial distribution of said refractive index is generated by incidence of said terahertz wave, wherein
    said terahertz-wave detection element is configured to detect a spatial-characteristics distribution which is generated in probe light irradiated to said electro-optic crystal layer in superposition with said terahertz wave and corresponds to a spatial distribution of a refractive index generated in said electro-optic crystal layer by incidence of said terahertz wave, thereby to detect said spatial intensity distribution of said incident terahertz wave, and an interposition layer consisting of an oxide and for causing a tensile stress to work on the electro-optic crystal layer is provided between said resin layer and said electro-optic crystal layer.

5. A method of manufacturing a terahertz-wave detection element capable of detecting a spatial intensity distribution that an incident terahertz wave has, the method comprising:

an oxide formation step of forming an oxide layer on one main surface of a first substrate consisting of an electro-optic crystal in which a refractive index at an incident position of a terahertz wave changes in accordance with incident intensity of said terahertz wave at the incident position, a joining step of joining said one main surface of said first substrate and a second substrate that supports said electro-optic crystal layer, by an adhesive consisting of a thermosetting resin, a polishing step of thinning said first substrate of a joined body obtained by said joining step, to a thickness equal to or larger than 1 µm and equal to or smaller than 30 µm by polishing said first substrate, a segmentation step of obtaining a large number of terahertz-wave detection elements by cutting said joined body into pieces of a predetermined element size, wherein in said oxide formation step, said oxide layer is formed such that said first substrate becomes convex to a side of said one main surface by causing a tensile stress to act on said first substrate, and in a thickness from 10 nm or more to 1 µm or less;

a total-reflection layer formation step of forming a total reflection layer consisting of a first dielectric multilayer film on a surface of said electro-optic crystal of said joined body after said polishing step; and a reflection-prevention layer formation step of forming a reflection prevention layer consisting of a second dielectric multilayer film on a surface of said second substrate of said joined body after said polishing step.

* * * * *